United States Patent
Pacetti

(10) Patent No.: US 8,791,171 B2
(45) Date of Patent: Jul. 29, 2014

(54) BIODEGRADABLE COATINGS FOR IMPLANTABLE MEDICAL DEVICES

(75) Inventor: Stephen D. Pacetti, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1358 days.

(21) Appl. No.: 12/023,953

(22) Filed: Jan. 31, 2008

(65) Prior Publication Data

US 2009/0149568 A1   Jun. 11, 2009

Related U.S. Application Data

(63) Continuation-in-part of application No. 10/428,691, filed on May 1, 2003, now Pat. No. 7,563,454.

(51) Int. Cl.
    *A61F 2/00*   (2006.01)
(52) U.S. Cl.
    USPC .......................... 523/113; 424/422; 424/423
(58) Field of Classification Search
    None
    See application file for complete search history.

(56) References Cited

U.S. PATENT DOCUMENTS

| | | |
|---|---|---|
| 2,968,649 A | 1/1961 | Pailthorp et al. |
| 3,051,677 A | 8/1962 | Rexford |
| 3,178,399 A | 4/1965 | Lo |
| 3,324,069 A | 6/1967 | Koblitz et al. |
| 3,779,805 A | 12/1973 | Alsberg |
| 3,856,827 A | 12/1974 | Cavitt |
| 4,076,929 A | 2/1978 | Dohany |
| 4,197,380 A | 4/1980 | Chao et al. |
| 4,304,010 A | 12/1981 | Mano |
| 4,346,710 A | 8/1982 | Thanawalla et al. |
| 4,353,960 A | 10/1982 | Endo et al. |
| 4,399,264 A | 8/1983 | Squire |
| 4,413,359 A | 11/1983 | Akiyama et al. |
| 4,423,183 A | 12/1983 | Close |
| 4,485,250 A | 11/1984 | Squire |
| 4,530,569 A | 7/1985 | Squire |
| 4,564,013 A | 1/1986 | Lilenfeld et al. |
| 4,569,978 A | 2/1986 | Barber |
| 4,632,842 A | 12/1986 | Karwoski et al. |
| 4,636,346 A | 1/1987 | Gold et al. |
| 4,718,907 A | 1/1988 | Karwoski et al. |
| 4,733,665 A | 3/1988 | Palmaz |
| 4,749,585 A | 6/1988 | Greco et al. |
| 4,754,009 A | 6/1988 | Squire |
| 4,770,939 A | 9/1988 | Sietsess et al. |
| 4,800,882 A | 1/1989 | Gianturco |
| 4,871,357 A | 10/1989 | Hsu et al. |
| 4,876,109 A | 10/1989 | Mayer et al. |
| 4,886,062 A | 12/1989 | Wiktor |
| 4,897,457 A | 1/1990 | Nakamura et al. |
| 4,908,404 A | 3/1990 | Benedict et al. |
| 4,910,276 A | 3/1990 | Nakamura et al. |
| 4,931,287 A | 6/1990 | Bae et al. |
| 4,935,477 A | 6/1990 | Squire |
| 4,948,851 A | 8/1990 | Squire |
| 4,973,142 A | 11/1990 | Squire |
| 4,975,505 A | 12/1990 | Squire |
| 4,977,008 A | 12/1990 | Squire |
| 4,977,025 A | 12/1990 | Squire |
| 4,977,026 A | 12/1990 | Squire |
| 4,977,297 A | 12/1990 | Squire |
| 4,977,901 A | 12/1990 | Ofstead |
| 4,982,056 A | 1/1991 | Squire |
| 4,985,308 A | 1/1991 | Squire |
| 4,999,248 A | 3/1991 | Squire |
| 5,000,547 A | 3/1991 | Squire |
| 5,006,382 A | 4/1991 | Squire |
| 5,030,394 A | 7/1991 | Sietses et al. |
| 5,047,020 A | 9/1991 | Hsu |
| 5,051,114 A | 9/1991 | Nemser et al. |
| 5,051,978 A | 9/1991 | Mayer et al. |
| 5,053,048 A | 10/1991 | Pinchuk |
| 5,076,659 A | 12/1991 | Bekiarian et al. |
| 5,093,427 A | 3/1992 | Barber |
| 5,107,852 A | 4/1992 | Davidson et al. |
| 5,110,645 A | 5/1992 | Matsumoto et al. |
| 5,112,457 A | 5/1992 | Marchant |
| 5,176,972 A | 1/1993 | Bloom et al. |
| 5,185,408 A | 2/1993 | Tang et al. |
| 5,246,451 A | 9/1993 | Trescony et al. |
| 5,276,121 A | 1/1994 | Resnick |
| 5,296,283 A | 3/1994 | Froggatt |
| 5,302,385 A | 4/1994 | Khan et al. |
| 5,308,685 A | 5/1994 | Froggatt |
| 5,310,838 A | 5/1994 | Hung et al. |
| 5,324,889 A | 6/1994 | Resnick |

(Continued)

FOREIGN PATENT DOCUMENTS

DE   19723723 A1   12/1998
EP   0568310 A1   11/1993

(Continued)

OTHER PUBLICATIONS

Barbakadze, V. et al. "Poly[3-(3,4-Dihydroxyphenyl)glyceric Acid]: A New Biologically Active Polymer from *Symphytum asperum* Lepeeh. and *S. caucasicum* Bieb.(*Boraginaceae*)", Molecules, 10, pp. 1135-1144. Sep. 30, 2005.*
U.S. Appl. No. 10/177,154, filed Jun. 21, 2002, Hossainy et al.
U.S. Appl. No. 10/198,912, filed Jul. 19, 2002, Ding et al.
U.S. Appl. No. 10/376,348, filed Feb. 26, 2003, Ding et al.
Anonymous, *Rolling Therapeutic Agent Loading Device for Therapeutic Agent Delivery of Coated Stent*, Research Disclosure, Publ., Hampshire, GB, No. 434, p. 975 (2000).
Arnold et al., *Effects of environment on the creep properties of a poly (ethylmethacrylate) based bone cement* J. Mater. Sci: Mater. In Med., vol. 12, pp. 707-717 (2001).
Bellex International, *CYTOP ®, Amorphous Fluorocarbon Polymer*, 1 page. (no date).
Bellex International, *Selected CYTOP Physical Data*, 1 page. (no date).
Bellex International, *CYTOP ®*, http://www.bellexinternational.com/cytop.htm, printed Mar. 30, 2001, 1 page.
Cifková et al., *Irritation effects of residual products derived from p(HEMA) gels*,Biomaterials, vol. 9, (Jul. 1998), pp. 372-375.

(Continued)

Primary Examiner — James Rogers
(74) Attorney, Agent, or Firm — Squire Patton Boggs (US) LLP

(57) ABSTRACT

Biodegradable coatings for implantable medical devices are disclosed.

3 Claims, No Drawings

(56) References Cited

U.S. PATENT DOCUMENTS

| | | | |
|---|---|---|---|
| 5,326,839 A | 7/1994 | Resnick | |
| 5,328,471 A | 7/1994 | Slepian | |
| 5,336,518 A | 8/1994 | Narayanan et al. | |
| 5,338,608 A | 8/1994 | Resnick | |
| 5,342,348 A | 8/1994 | Kaplan | |
| 5,353,368 A | 10/1994 | Resnick | |
| 5,354,910 A | 10/1994 | Hung et al. | |
| 5,368,566 A | 11/1994 | Crocker | |
| 5,380,299 A | 1/1995 | Fearnot et al. | |
| 5,383,853 A | 1/1995 | Jung et al. | |
| 5,383,928 A | 1/1995 | Scott et al. | |
| 5,395,311 A | 3/1995 | Andrews | |
| 5,403,341 A | 4/1995 | Solar | |
| 5,408,020 A | 4/1995 | Hung et al. | |
| 5,417,969 A | 5/1995 | Hsu et al. | |
| 5,443,458 A | 8/1995 | Eury | |
| 5,447,724 A | 9/1995 | Helmus et al. | |
| 5,455,040 A | 10/1995 | Marchant | |
| 5,464,650 A | 11/1995 | Berg et al. | |
| 5,545,208 A | 8/1996 | Wolff et al. | |
| 5,560,463 A | 10/1996 | Link et al. | |
| 5,562,734 A | 10/1996 | King | |
| 5,569,463 A | 10/1996 | Helmus et al. | |
| 5,575,818 A | 11/1996 | Pinchuk | |
| 5,578,073 A | 11/1996 | Haimovich et al. | |
| 5,584,877 A | 12/1996 | Miyake et al. | |
| 5,591,224 A | 1/1997 | Schwartz et al. | |
| 5,604,283 A | 2/1997 | Wada et al. | |
| 5,605,696 A | 2/1997 | Eury et al. | |
| 5,616,608 A | 4/1997 | Kinsella et al. | |
| 5,628,728 A | 5/1997 | Tachibana et al. | |
| 5,632,771 A | 5/1997 | Boatman et al. | |
| 5,632,776 A | 5/1997 | Kurumatani et al. | |
| 5,632,840 A | 5/1997 | Campbell | |
| 5,635,201 A | 6/1997 | Fabo | |
| 5,667,767 A | 9/1997 | Greff et al. | |
| 5,670,558 A | 9/1997 | Onishi et al. | |
| 5,679,400 A | 10/1997 | Tuch | |
| 5,684,061 A | 11/1997 | Ohnishi et al. | |
| 5,691,311 A | 11/1997 | Maraganore et al. | |
| 5,697,967 A | 12/1997 | Dinh et al. | |
| 5,700,286 A | 12/1997 | Tartaglia et al. | |
| 5,713,949 A | 2/1998 | Jayaraman | |
| 5,716,981 A | 2/1998 | Hunter et al. | |
| 5,750,234 A | 5/1998 | Johnson et al. | |
| 5,758,205 A | 5/1998 | Hara et al. | |
| 5,759,205 A | 6/1998 | Valentini | |
| 5,760,118 A | 6/1998 | Sinclair et al. | |
| 5,766,710 A * | 6/1998 | Turnlund et al. | 623/1.15 |
| 5,776,184 A | 7/1998 | Tuch | |
| 5,804,318 A | 9/1998 | Pinchuk et al. | |
| 5,820,917 A | 10/1998 | Tuch | |
| 5,824,048 A | 10/1998 | Tuch | |
| 5,824,049 A | 10/1998 | Ragheb et al. | |
| 5,827,587 A | 10/1998 | Fukushi | |
| 5,830,178 A | 11/1998 | Jones et al. | |
| 5,837,008 A | 11/1998 | Berg et al. | |
| 5,837,313 A | 11/1998 | Ding et al. | |
| 5,851,508 A | 12/1998 | Greff et al. | |
| 5,858,746 A | 1/1999 | Hubbell et al. | |
| 5,858,990 A | 1/1999 | Walsh | |
| 5,860,963 A | 1/1999 | Azam et al. | |
| 5,861,168 A | 1/1999 | Cooke et al. | |
| 5,865,814 A | 2/1999 | Tuch | |
| 5,869,127 A | 2/1999 | Zhong | |
| 5,873,904 A | 2/1999 | Ragheb et al. | |
| 5,874,165 A | 2/1999 | Drumheller | |
| 5,879,697 A | 3/1999 | Ding et al. | |
| 5,897,911 A | 4/1999 | Loeffler | |
| 5,900,425 A | 5/1999 | Kanikanti et al. | |
| 5,911,704 A | 6/1999 | Humes | |
| 5,921,933 A | 7/1999 | Sarkis et al. | |
| 5,922,393 A | 7/1999 | Jayaraman | |
| 5,928,279 A | 7/1999 | Shannon et al. | |
| 5,932,299 A | 8/1999 | Katoot | |
| 5,945,115 A | 8/1999 | Dunn et al. | |
| 5,971,954 A | 10/1999 | Conway et al. | |
| 5,980,928 A | 11/1999 | Terry | |
| 5,980,972 A | 11/1999 | Ding | |
| 5,997,517 A | 12/1999 | Whitbourne | |
| 6,015,541 A | 1/2000 | Greff et al. | |
| 6,033,724 A | 3/2000 | Molitor | |
| 6,042,875 A | 3/2000 | Ding et al. | |
| 6,051,648 A | 4/2000 | Rhee et al. | |
| 6,056,993 A | 5/2000 | Leidner et al. | |
| 6,060,451 A | 5/2000 | DiMaio et al. | |
| 6,060,534 A | 5/2000 | Ronan et al. | |
| 6,080,488 A | 6/2000 | Hostettler et al. | |
| 6,090,134 A | 7/2000 | Tu et al. | |
| 6,096,070 A | 8/2000 | Ragheb et al. | |
| 6,096,396 A | 8/2000 | Patton et al. | |
| 6,096,798 A | 8/2000 | Luthra et al. | |
| 6,096,809 A | 8/2000 | Lorcks et al. | |
| 6,099,562 A | 8/2000 | Ding et al. | |
| 6,099,563 A | 8/2000 | Zhong | |
| 6,110,188 A | 8/2000 | Narciso, Jr. | |
| 6,110,483 A | 8/2000 | Whitbourne et al. | |
| 6,113,629 A | 9/2000 | Ken | |
| 6,120,536 A | 9/2000 | Ding et al. | |
| 6,120,904 A | 9/2000 | Hostettler et al. | |
| 6,121,027 A | 9/2000 | Clapper et al. | |
| 6,124,045 A | 9/2000 | Soda et al. | |
| 6,129,761 A | 10/2000 | Hubbell | |
| 6,153,252 A | 11/2000 | Hossainy et al. | |
| 6,165,212 A | 12/2000 | Dereume et al. | |
| 6,179,817 B1 | 1/2001 | Zhong | |
| 6,197,051 B1 | 3/2001 | Zhong | |
| 6,203,551 B1 | 3/2001 | Wu | |
| 6,214,901 B1 | 4/2001 | Chudzik et al. | |
| 6,224,894 B1 | 5/2001 | Jamiolkowski et al. | |
| 6,231,590 B1 | 5/2001 | Slaikeu et al. | |
| 6,242,041 B1 | 6/2001 | Katoot et al. | |
| 6,254,632 B1 | 7/2001 | Wu et al. | |
| 6,258,121 B1 | 7/2001 | Yang et al. | |
| 6,262,034 B1 | 7/2001 | Mathiowitz et al. | |
| 6,273,913 B1 | 8/2001 | Wright et al. | |
| 6,299,604 B1 | 10/2001 | Ragheb et al. | |
| 6,344,035 B1 | 2/2002 | Chudzik | |
| 6,362,271 B1 | 3/2002 | Lin et al. | |
| 6,408,878 B2 | 6/2002 | Unger et al. | |
| 6,410,612 B1 | 6/2002 | Hatanaka | |
| 6,464,683 B1 | 10/2002 | Samuelson et al. | |
| 6,503,556 B2 | 1/2003 | Harish et al. | |
| 6,545,097 B2 | 4/2003 | Pinchuk et al. | |
| 6,551,708 B2 | 4/2003 | Tsuda et al. | |
| 6,716,444 B1 | 4/2004 | Castro et al. | |
| 6,746,773 B2 | 6/2004 | Llanos et al. | |
| 7,005,137 B1 | 2/2006 | Hossainy et al. | |
| 7,094,256 B1 | 8/2006 | Shah et al. | |
| 7,217,426 B1 | 5/2007 | Hossainy | |
| 7,244,443 B2 | 7/2007 | Pacetti | |
| 7,247,313 B2 | 7/2007 | Roorda et al. | |
| 2001/0014717 A1 | 8/2001 | Hossainy et al. | |
| 2001/0029351 A1 | 10/2001 | Falotico et al. | |
| 2002/0051730 A1 | 5/2002 | Bodnar et al. | |
| 2002/0090389 A1 | 7/2002 | Humes et al. | |
| 2002/0094440 A1 | 7/2002 | Llanos et al. | |
| 2002/0099438 A1 | 7/2002 | Furst | |
| 2002/0111590 A1 | 8/2002 | Davila et al. | |
| 2002/0122877 A1 | 9/2002 | Harish et al. | |
| 2002/0123801 A1 | 9/2002 | Pacetti et al. | |
| 2002/0133183 A1 | 9/2002 | Lentz et al. | |
| 2002/0143386 A1 | 10/2002 | Davila et al. | |
| 2002/0165608 A1 | 11/2002 | Llanos et al. | |
| 2002/0188037 A1 | 12/2002 | Chudzik et al. | |
| 2003/0004563 A1 | 1/2003 | Jackson et al. | |
| 2003/0031780 A1 | 2/2003 | Chudzik et al. | |
| 2003/0039689 A1 | 2/2003 | Chen et al. | |
| 2003/0060877 A1 | 3/2003 | Falotico et al. | |
| 2003/0065346 A1 | 4/2003 | Evens et al. | |
| 2003/0065377 A1 | 4/2003 | Davila et al. | |
| 2003/0073961 A1 | 4/2003 | Happ | |
| 2003/0077312 A1 | 4/2003 | Schmulewicz et al. | |

(56) References Cited

U.S. PATENT DOCUMENTS

| | | | |
|---|---|---|---|
| 2004/0063805 A1 | 4/2004 | Pacetti et al. | |
| 2004/0102758 A1 | 5/2004 | Davila et al. | |
| 2005/0288398 A1 | 12/2005 | Messersmith et al. | |

FOREIGN PATENT DOCUMENTS

| | | |
|---|---|---|
| EP | 0623354 A1 | 11/1994 |
| EP | 0633032 A1 | 1/1995 |
| EP | 0 665 023 | 8/1995 |
| EP | 0747069 A2 | 12/1996 |
| EP | 0815803 A1 | 1/1998 |
| EP | 0893108 A2 | 1/1999 |
| EP | 0950385 A2 | 10/1999 |
| EP | 0950386 A2 | 10/1999 |
| EP | 0 970 711 | 1/2000 |
| EP | 0968688 A1 | 1/2000 |
| EP | 0997115 A2 | 5/2000 |
| EP | 1 023 879 | 8/2000 |
| EP | 1 192 957 | 4/2002 |
| WO | WO 92/05695 | 4/1992 |
| WO | WO 92/18320 | 10/1992 |
| WO | WO 94/02185 | 2/1994 |
| WO | WO 96/21404 | 7/1996 |
| WO | WO 97/41164 | 11/1997 |
| WO | WO 98/08463 | 3/1998 |
| WO | WO 98/13405 | 4/1998 |
| WO | WO 98/36784 | 8/1998 |
| WO | WO 98/58680 | 12/1998 |
| WO | WO 99/32051 | 7/1999 |
| WO | WO 99/55396 | 11/1999 |
| WO | WO 00/02599 | 1/2000 |
| WO | WO 00/12147 | 3/2000 |
| WO | WO 00/27455 | 5/2000 |
| WO | WO 00/29043 | 5/2000 |
| WO | WO 00/32255 | 6/2000 |
| WO | WO 00/38754 | 7/2000 |
| WO | WO 00/41738 | 7/2000 |
| WO | WO 00/64506 | 11/2000 |
| WO | WO 01/01890 | 1/2001 |
| WO | WO 01/30403 A1 | 5/2001 |
| WO | WO 01/49340 | 7/2001 |
| WO | WO 01/87342 A2 | 11/2001 |
| WO | WO 01/87368 | 11/2001 |
| WO | WO 01/87372 | 11/2001 |
| WO | WO 01/87376 A1 | 11/2001 |
| WO | WO 02/24249 | 3/2002 |
| WO | WO 02/26139 A1 | 4/2002 |
| WO | WO 02/26271 A | 4/2002 |
| WO | WO 02/26281 A1 | 4/2002 |
| WO | WO 02/47731 | 6/2002 |
| WO | WO 02/47732 | 6/2002 |
| WO | WO 03/022324 | 3/2003 |
| WO | WO 2008/019352 | 2/2008 |

OTHER PUBLICATIONS

Dalsin et al., *DOPA: A New Anchor for PEGylation of Biomaterial Surfaces*, Soc. For Biomaterials 28th Annual Meeting Transactions, pp. 40 (2002).
Deb et al., *Effect of crosslinking agents on poly(ethylmethacrylate) bone cements*, J. of Mater.Sci: Mater. In Med., vol. 8, pp. 829-833 (1997).
3M, *Specialty Fluids 3M™ Fluorinert™ Liquids, Typical Properties*, http://www.3m.com/market/industrial/fluids/fluoprop.html, printed Mar. 30, 2001, 3 pages.
Del Guerra et al., *In vitro biocompatibility of fluorinated polyurethanes*, J. Mater. Sci. In Med., vol. 5, pp. 452-456 (1994).
DuPont, *Available Grades of DuPont Teflon® AF*, Teflon Amorphous Fluoropolymer, http://www.dupont.com/teflon/af/grades.html, printed Sep. 21, 2004, 2 pages.
DuPont, *High-Performance/Potential Applications*, Teflon Amorphous Fluoropolymer, http://www.dupont.com/teflon/af/potapps.html, printed Mar. 30, 2001, 3 pages.
DuPont, *Performance Comparison of Teflon AF*, Teflon Amorphous Fluoropolymer, http://www.dupont.com/teflon/af/performance.html, printed Mar. 30, 2001, 3 pages.
DuPont, *Processing of Teflon® AF*, Teflon Amorphous Fluoropolymer, http://www.dupont.com/teflon/af/processing.html, printed Mar. 30, 2001, 1 page.
DuPont, Sales Notice, Teflon Amorphous Fluoropolymer, http://www.dupont.com/teflon/af/patent.html, printed Sep. 21, 2004, 2 pages.
DuPont, *Teflon AF 1601S amorphous fluoropolymer solutions*, product information, 2 pages. (1998).
DuPont, *Teflon® AF amorphous fluoropolymers*, Product Information, 6 pages. (1998).
DuPont, *Teflon® AF: A New Generation of High-Performance Fluoropolymer Resins*, http://www.dupont.com/teflon/af/index.html, printed Mar. 30, 2001, 1 page.
DuPont, *Teflon® Protects Superconductors Against Acid*, Teflon Amorphous Fluoropolymer, http://www.dupont.com/teflon/af/superconductor.html, printed Sep. 21, 2004, 2 pages.
DuPont, *Unique Properties of Teflon® AF*, Teflon Amorphous Fluoropolymer, http://www.dupont.com/teflon/af/unique.html, printed Mar. 30, 2001, 3 pages.
Fine et al., *Improved nerve regeneration through piezoelectric vinylidene fluoride-trifluoroethylene copolymer guidance channels*, Biomaterials, vol. 12, Oct. 1991, pp. 775-780.
Fischell, *Polymer Coatings for Stents*, Circulation, 94:1494-95 (1996).
Gullickson, *Reference Data Sheet on Common Chlorinated Solvents*, http://www.mcs.net/~hutter/tee/chlorina.html, printed Mar. 30, 2001, 5 pages.
Gunn et al., *Stent coatings and local drug delivery*, Eur. Heart J., vol. 20, issue 23, pp. 1693-1700 (1999).
Harper et al., *Fatigue Characteristics of Polyethylmethacrylate Based Bone Cement Reinforced with Silane Coupled Hydroxyapatite*, Fifth World Biomaterials Congress, May 29-Jun. 2, 1996, Toronto, Canada, Abstract 351, 3 pgs.
Harper et al., *Mechanical properties of hydroxyapatite reinforced poly (ethyl methacrylate) bone cement after immersion in a physiological solution: influence of a silane coupling agent*, J. Mater. Sci.: Mater. In Med., vol. 11, pp. 491-497 (2000).
International Search Report for WIPO appl. WIPO/US03/15347, filed May 14, 2003, date of mailing Sep. 4, 2003, 6 pgs.
International Search Report for WIPO appl. WIPO/US03/15544, filed May 14, 2003, date of mailing Jan. 23, 2004, 9 pgs.
International Search Report for WIPO appl. WIPO/US03/21170, filed Jul. 2, 2003, date of mailing Oct. 31, 2003, 8 pgs.
International Search Report for WIPO appl. WIPO/US03/28643, filed Sep. 10, 2003, date of mailing Mar. 12, 2003, 10 pgs.
Kruft et al., *Studies on radio-opaque polymeric biomaterials with potential applications to endovascular prostheses*, Biomaterials, vol. 17, No. 18, pp. 1803-1812 (1996).
Lambert et al., *Localized Arterial Wall Drug Delivery From a Polymer-Coated Removable Metallic Stent*, Circulation, vol. 90, No. 2, pp. 1003-1011 (1994).
Laroche et al., *Polyvinylidene fluoride (PVDF) as a biomaterial: From polymeric raw material to monofilament vascular suture*, J. of Biomedical Mat. Research, vol. 29, pp. 1525-1536 (1995).
Lin et al., *Fluropolymer Alloys Performance Optimization of PVDF Alloys*, Fluoropolymers 2 Properties, edited by Hougham et al., Plenum Publishers N.Y. pp. 121-136 (1999).
Lin et al., *Surface characterization and platelet adhesion studies on fluorocarbons prepared by plasma-induced graft polymerization*, J. Biomater Sci. Polymer Edn., vol. 11, No. 7, pp. 701-714 (2000).
Luthra, Biointeractions Ltd (BIL), http://www.biomateria.com/biointeractions.html, printed Sep. 21, 2004, 3 pages.
Materials Engineering, *Applications in Design/Manufacturing/R&D*, Materials Selector 1993, Penton Publishing (1992) 6 pgs.
Medtronic, Trillium Affinity NT, Oxygenator, Product Information, 6 pages. (2000).
NCMS SOLV-DB, *Query Results for: CFC*, http://solvdb.ncms.org/CAT01.idc?chemcat=CFC, printed Mar. 30, 2001, 2 pages.
NCMS SOLV-DB, *Query Results for: FC-75 Fluorinert*, http://solvdb.ncms.org/common01.idc, printed Mar. 30, 2001, 2 pages.

(56) References Cited

OTHER PUBLICATIONS

Novick et al., *Protein-containing hydrophobic coatings and films*, Biomaterials, vol. 23, No. 2 (2002) pp. 441-448.
Parkell, Inc., *Material Safety Data Sheets*, http://www.parkell.com/msds.html, printed Oct. 21, 2004, 2 pgs.
Parkell, Inc., *MSDS No: S426, VAR, Material Safety Data Sheet*, 2 pgs (2002).
Parkell, Inc., MSDS No: S441, Material Safety Data Sheet, 2 pgs (2002).
Parkell, Inc., *SNAP Powder-Liquid Temporary Crown and Bridge Resin*, http://www.parkell.com/snap.html, printed Oct. 21, 2004, 1 pg.
Porté-Durrieu et al., *Development of "Heparin-Like" Polymers Using Swift Heavy Ion and Gamma Radiation. I. Preparation and Characterization of the Materials*, Surface Treatment of Biomaterials, pp. 119-127 (2000).
Porté-Durrieu et al., *Surface Treatment of Biomaterials by Gamma and Swift Heavy Ions Grafting*, Nuclear Instruments and Methods in Physics Research, vol. B 151, pp. 404-415 (1999).
Revell et al., *Experimental Studies of the Biological Response to a New Bone Cement: II Soft Tissue Reactions in the Rat*, Clinical Materials, vol. 10, pp. 233-238 (1992).
Techspray, Bulk Solvents, http://www.techspray.com/bulksup.htm, printed Sep. 21, 2004, 3 pages.
Techspray, *Flux Remover AMS*, Product Information, http://www.techspray.com/1665info.htm, printed Aug. 28, 2001, 2 pages.
Teomin et al., *Perivascular delivery of heparin for the reduction of smooth muscle cell proliferation after endothelial injury*, J. of Controlled Release, vol. 60, pp. 129-142 (1999).
The condensed Chemical Dictionary $10^{th}$ ed., Van Nostrand Reinhold Co. pp. 32, 198 (1981).
The Encyclopedia of Chemical Technology $5^{th}$ ed., John Wiley &Sons, Inc. pp. 764-767 (1993).
Topol et al., *Frontiers in Interventional Cardiology*, Circulation, vol. 98, pp. 1802-1820 (1998).
Urban et al., *Why Make Monofilament Sutures Out of Polyvinylidene Fluoride?*, ASAIO J., vol. 40, No. 2, pp. 145-156 (1994).
Verweire et al., *Evaluation of fluorinated polymers as coronary stent coating*, J. Mater.Sci: Mater. In Med., vol. 11, No. 4, pp. 207-212 (2000).
Weightman et al., *The Mechanical Properties of Cement and Loosening of the Femoral Component of Hip Replacements*, J. Bone and Joint Surg., vol. 69-B, No. 4, pp. 558-564 (Aug. 1987).
Wholey et al., *Global Experience in Cervical Carotid Artery Stent Placement*, Catherization and Cardiovascular Inteventions, vol. 50, No. 2, pp. 160-167 (2000).
Woo et al., *Phase Behavior of Polycarbonate Blends with Selected Halogenated Polymers*, J. Appl. Polym. Sci., vol. 30, pp. 4243-4249 (1985).
International Search Report for PCT/US2009/031691, mailed Apr. 22, 2010, 10 pgs.

\* cited by examiner

BIODEGRADABLE COATINGS FOR IMPLANTABLE MEDICAL DEVICES

RELATED APPLICATION

This application is a continuation-in-part of U.S. patent application Ser. No. 10/428,691 which was filed on May 1, 2003.

FIELD OF THE INVENTION

The present invention is directed to biodegradable coatings for implantable medical devices.

BACKGROUND OF THE INVENTION

The traditional method of administering therapeutic agents to treat diseases of the internal organs and vasculature has been by systemic delivery. Systemic delivery involves administering a therapeutic agent at a discrete location followed by the agent migrating throughout the patient's body including, of course, to the afflicted organ or area of the vasculature. But to achieve a therapeutic amount of the agent at the afflicted site, an initial dose substantially greater than the therapeutic amount must be administered to account for the dilution the agent undergoes as it travels through the body. Systemic delivery introduces the therapeutic agent in two ways: into the digestive tract (enteral administration) or into the vascular system (parenteral administration), either directly, such as injection into a vein or an artery, or indirectly, such as injection into a muscle or into the bone marrow. Absorption, distribution, metabolism, excretion and toxicity, the ADMET factors, strongly influence delivery by each of these routes. For enteric administration, factors such as a compound's solubility, its stability in the acidic environs of the stomach and its ability to permeate the intestinal wall all affect drug absorption and therefore its bioavailability. For parenteral delivery, factors such as enzymatic degradation, lipophilic/hydrophilic partitioning coefficient, lifetime in circulation, protein binding, etc. will affect the agent's bioavailability.

At the other end of the spectrum is local delivery, which comprises administering the therapeutic agent directly to the afflicted site. With localized delivery, the ADMET factors tend to be less important than with systemic administration because administration is essentially directly to the treatment site. Thus, the initial dose can be at or very close to the therapeutic amount. With time, some of the locally delivered therapeutic agent may diffuse over a wider region, but that is not the intent of localized delivery, and the diffused portion's concentration will ordinarily be sub-therapeutic, i.e., too low to have a therapeutic effect. Nevertheless, localized delivery of therapeutic agents is currently considered a state-of-the-art approach to the treatment of many diseases such as cancer and atherosclerosis.

Localized delivery of therapeutic agents may be accomplished using implantable medical devices. Coating implantable medical devices with therapeutic agents, however, is not without problems.

The family of mussel adhesive proteins is unique in that they bond to a large variety of substrates in an aqueous environment. These proteins share numerous molecular motifs, however, approximately 25% of amino acids in a particular mussel adhesive protein is the modified amino acid 3,4-dihydroxyphenyl-L-alanine (DOPA). It has further been determined that mussel adhesion to rocks, wood and metal is due in large part to DOPA. It has been found, however, that the portion of DOPA responsible for the remarkable adhesive capability of these polymers is the 3,4-dihydroxyphenyl group. The present invention takes advantage of the strong binding properties of 3,4-dihydroxyphenyl, and 2,3-dihydroxyphenyl, to provide novel biodegradable coatings, primarily for use as primer coatings for implantable medical devices, particularly bare metal implantable medical devices.

SUMMARY

The present invention relates to a biodegradable coating for an implantable medical device that includes a biodegradable polymer functionalized with an ortho-dihydroxyphenyl compound, the overall structure having the formula:

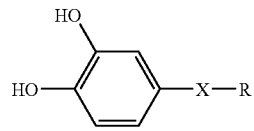

where X is a linker group and R is the biodegradable polymer.

In various aspects, R includes a polyester which can be selected from a group that includes a poly(glycolide), poly (D,L-lactide), poly(L-lactide), poly(D,L-lactide-co-glycolide), poly(caprolactone), poly(dioxanone), poly(glycolide-co-trimethylenecarbonate) and copolymers thereof.

In various aspects, R includes a poly(esteramide), poly (tyrosine-derived carbonate), a poly(tyrosine-derived ester), a poly(tyrosine-α-hydroxyacid), a poly(orthoester) or a biodegradable polyurethane.

In various aspects, R includes a poly(depsipeptide) which in some aspects can have the general formula:

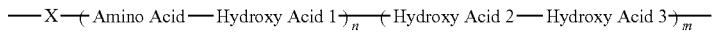

where X is the linker group. In this aspect, the amino acid can be selected from the group consisting of aspartic acid, glutamic acid, lysine, cysteine, serine, threonine and tyrosine. In this aspect, hydroxy acid 1, hydroxy acid 2 and hydroxy acid 3 can be independently selected from a group that includes glycolic acid, L-lactic acid, D-lactic acid, D,L-lactic acid, meso-lactic acid, caprolactone, dioxanone, β-butyrolactone, β-propiolactone and β-valerolactone.

In various aspects, the linker group can include between 1 and 16 carbon atoms.

In various aspects, the linker group is linear, branched, unsaturated or cycloaliphatic. In various aspects, the linker group comprises an ester, an amide, an ether, an anhydride, a sulfoester, a thioether, a sulfone, a phosphonate, a phosphoester, a carbonate, an imino-carbonate, an acetal, a ketal, an imine, an ortho-ester, a sulfamide or a urethane bond.

In various aspects, the biodegradable polymer can be functionalized with two ortho-dihydroxyphenyl compounds, the overall structure having the formula:

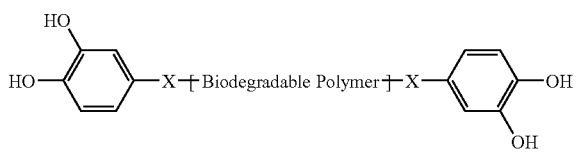

where X independently comprises a linear, branched, unsaturated or cycloaliphatic linker.

In various aspects, the biodegradable polymer can be functionalized with multiple ortho-dihydroxyphenyl compounds, the overall structure having the formula:

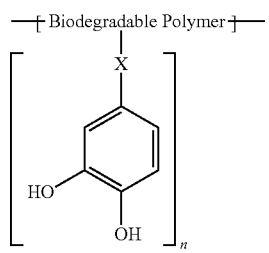

where X independently comprises a linear, branched, unsaturated or cycloaliphatic linker.

Another aspect of the invention relates to an implantable medical device that includes a coating according to the invention. The implantable medical device can be a stent.

DETAILED DESCRIPTION

The present invention provides a biodegradable coating for an implantable medical device that includes a biodegradable polymer functionalized with an ortho-dihydroxyphenyl compound, the overall structure having formula I:

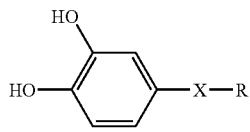

where X is a linker group and R is the biodegradable polymer.

In various aspects, a biodegradable polymer can be functionalized with a different ortho-dihydroxyphenyl compound, the overall structure having formula II:

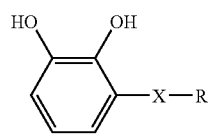

where X is a linker group and R is the biodegradable polymer.

It is to be understood that both of the ortho-dihydroxyphenyl compounds depicted by formulas I and II above are suitable for coatings of the present invention although compounds with the structure according to formula I are presently preferred.

As used herein, "biodegradable" refers to materials that are capable of being degraded or absorbed when exposed to bodily fluids such as blood, and components thereof such as enzymes or oxidative species, and that can be gradually absorbed and/or eliminated by the body.

In various aspects, R includes a polyester which can be selected from a group that includes a poly(glycolide), poly (D,L-lactide), poly(L-lactide), poly(D,L-lactide-co-glycolide), poly(caprolactone), poly(dioxanone), poly(glycolide-co-trimethylenecarbonate) and copolymers thereof.

When the biodegradable coating is used as a primer layer on an implantable medical device and a drug reservoir layer is disposed over the primer layer, the R group can be chosen to be compatible with the reservoir layer polymer. For example, if a drug reservoir layer includes poly(D,L-lactide), then a primer layer would be chosen, without limitation, to also include poly(D,L-lactide), an example of which is shown by formula III.

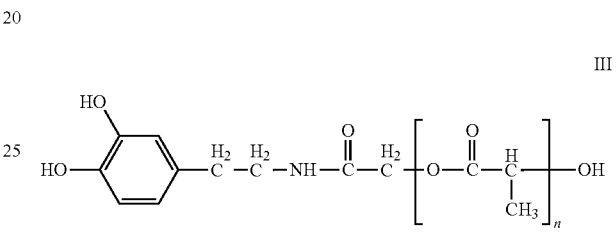

The synthesis of this polymer involves ring-opening polymerization using D,L-lactide and glycolic acid as the initiator. This yields an acid functional poly(D,L-lactide). Dopamine is then coupled to the carboxyl endgroup, methods of which are known to those skilled in the art.

The polymer of formula III can attach to a metal surface, e.g., a bare metal stent, by ortho-dihydroxyphenyl endpoint attachment. If the polyester polymer segment is too large however, it is unlikely that the ortho-dihydroxyphenyl would effectively coordinate with the metal surface. Thus, the polymer will be chosen to be less than 20,000 Daltons.

In an alternative embodiment, an ortho-dihydrophenyl moiety can be present at both termini of a biodegradable polymer, as shown by formula IV:

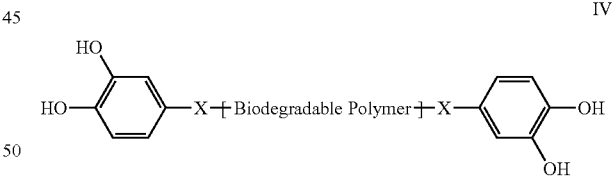

Synthesis of this moiety can be accomplished using methods known to those skilled in the art, such as that depicted below:

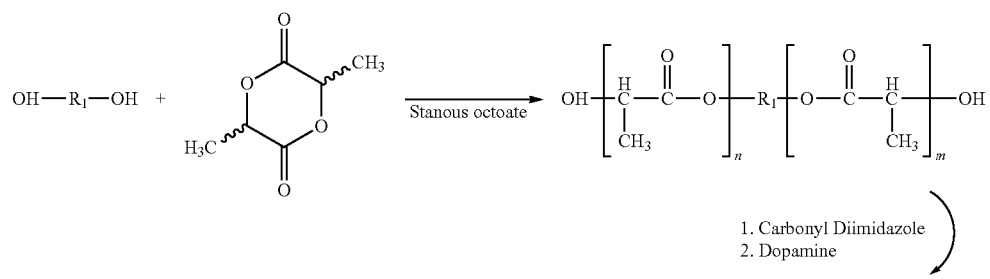

-continued

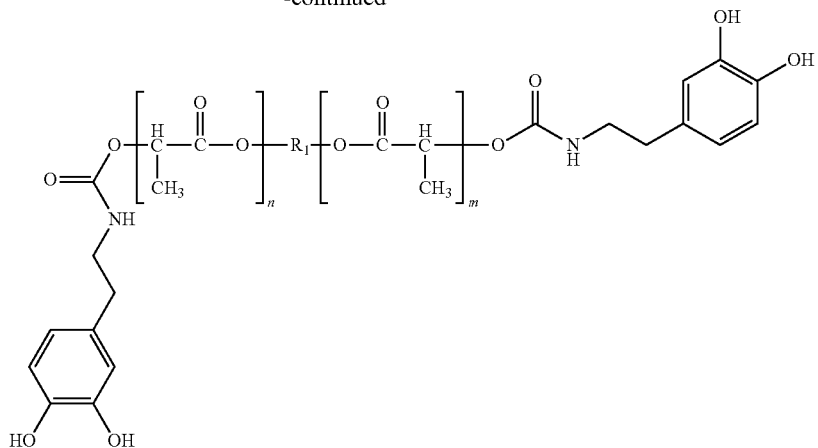

In this pathway, $R_1$ may be a $C_2$ to $C_{16}$ linear, branched, unsaturated or cyclic hydrocarbon. When this structure is used as a primer coating for a metal implantable device, the two ortho-dihydroxyphenyl moieties will attach to the device surface, thereby forming a loop-like structure on the device.

Biodegradable primers containing a much higher number of ortho-dihydroxy phenyl groups are also encompassed by the present invention. For example, the biodegradable polymer can be functionalized with multiple ortho-dihydroxyphenyl compounds having an overall structure with the formula:

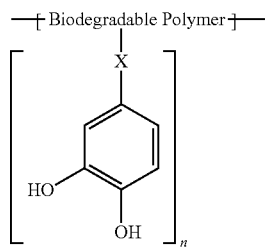

where X independently comprises a linear, branched, unsaturated or cycloaliphatic linker. In this aspect, the ortho-dihydroxyphenyl moieties can be attached to the biodegradable polymer as grafts or as pendant groups.

Similarly, a poly(depsipeptide) wherein the amino acid is aspartic acid, glutamic acid or lysine are possible according to the invention. As used herein, "poly(depsipeptide)" refers to a polypeptide in which one or more of the amide bonds are replaced by ester bonds. An exemplary poly(depsipeptide) is depicted by formula V below:

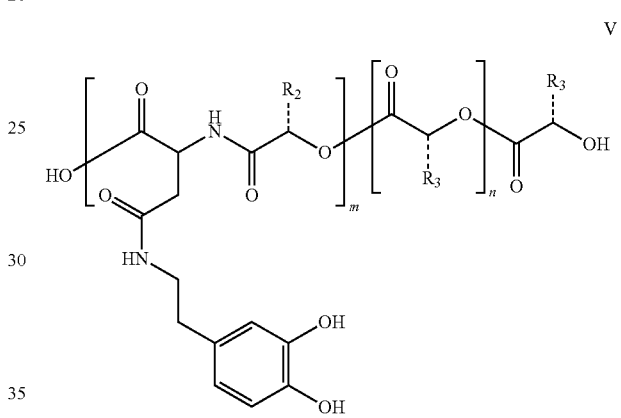

In this aspect of the invention, $R_2$ and $R_3$ can independently be either hydrogen or a methyl group. This structure allows for any number of ortho-dihydroxyphenyl groups up to that matching the monomer number "m". In this family of poly (depsipeptides), two cyclic monomers are used to produce the polymer. One monomer bears the protected amino acid side chain that is used to conjugate the dopamine or other ortho-dihydroxyphenyl group. The second cyclic monomer is a conventional ring opening monomer such as glycolide, lactide, dioxanone, β-butyrolactone, β-propiolactone or caprolactone. A schematic showing presently preferred amino acids and hydroxyl acids in the first block and the possible ring opening monomers in the second block is depicted below:

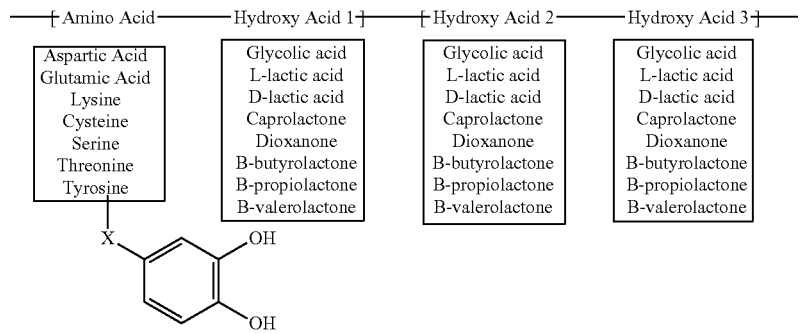

| Amino Acid | Hydroxy Acid 1 | Hydroxy Acid 2 | Hydroxy Acid 3 |
|---|---|---|---|
| Aspartic Acid<br>Glutamic Acid<br>Lysine<br>Cysteine<br>Serine<br>Threonine<br>Tyrosine | Glycolic acid<br>L-lactic acid<br>D-lactic acid<br>Caprolactone<br>Dioxanone<br>B-butyrolactone<br>B-propiolactone<br>B-valerolactone | Glycolic acid<br>L-lactic acid<br>D-lactic acid<br>Caprolactone<br>Dioxanone<br>B-butyrolactone<br>B-propiolactone<br>B-valerolactone | Glycolic acid<br>L-lactic acid<br>D-lactic acid<br>Caprolactone<br>Dioxanone<br>B-butyrolactone<br>B-propiolactone<br>B-valerolactone |

In this aspect, hydroxy acid 1, hydroxy acid 2 and hydroxy acid 3 can be independently selected from a group that includes glycolic acid, L-lactic acid, D-lactic acid, caprolactone, dioxanone, β-butyrolactone, β-propiolactone and β-valerolactone. These amino acids include those with R-groups that could be used for attachment of an ortho-dihydroxyphenyl group. Aspartic acid, glutamic acid and lysine are presently preferred.

An ortho-dihydroxyphenyl group of the invention can also be added to other biodegradable polymers including poly(esteramides), poly(tyrosine-derived carbonates), poly(tyrosine-derived esters), poly(tyrosine-alphahydroxyacids) and biodegradable polyurethanes.

An example of a poly(tyrosine-derived carbonate) wherein the ortho-dihydroxyphenyl group is present as a conjugated dopamine and the amount of ortho-dihydroxyphenyl can be adjusted by varying the ratio of "m" to "n" is depicted by formula VI.

As in formula VI above, the amount of ortho-dihydroxyphenyl substitution can be controlled by the amount of the first monomer. $R_1$ may be any $C_1$ to $C_{16}$ linear, branched, cycloaliphatic, aromatic, unsaturated hydrocarbon, poly(ethylene glycol), poly(propylene glycol), or poly(tetramethylene gycol). Methods of synthesizing this type of poly(tyrosine-derived ester) are known to those skilled in the art.

It is to be understood that while the biodegradable coatings of the invention are primarily intended to be used as primer layers on an implantable medical device, they also may serve as drug reservoir layers.

Another aspect of the invention relates to an implantable medical device comprising a coating according to the invention.

As used herein, "implantable medical device" refers to any type of appliance that is totally or partly introduced, surgically or medically, into a patient's body or by medical intervention into a natural orifice, and which is intended to remain

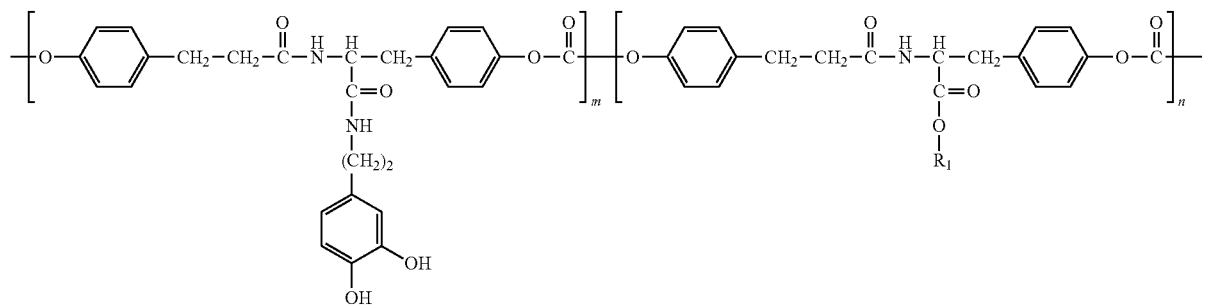

VI $R_1$ can be any $C_1$ to $C_{16}$ linear, branched, cycloaliphatic, aromatic or unsaturated hydrocarbon. Methods of synthesizing the precursor to the compound of formula VI are known in the art.

An example of a poly(tyrosine-derived ester) is depicted by formula VII.

there after the procedure. The duration of implantation may be essentially permanent, i.e., intended to remain in place for the remaining lifespan of the patient; until the device biodegrades; or until it is physically removed. Examples of implantable medical devices include, without limitation, implantable cardiac pacemakers and defibrillators, leads and

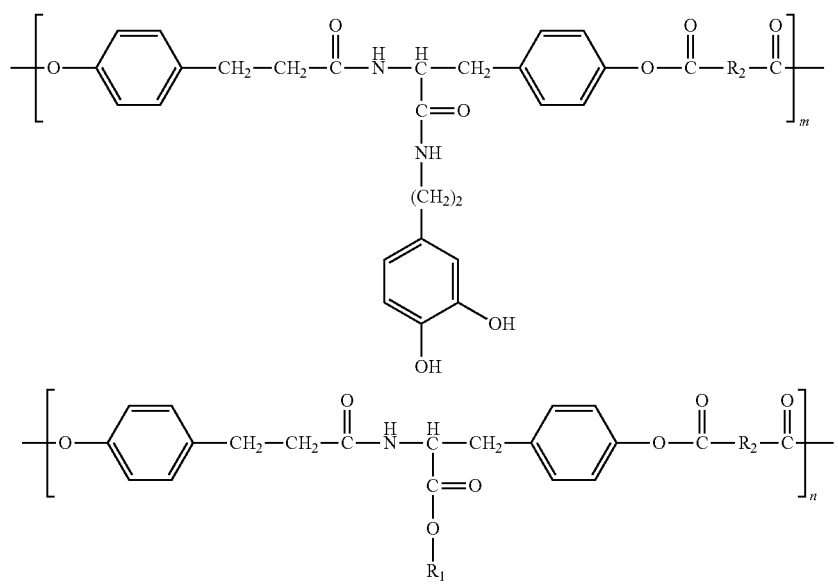

VII electrodes for the preceding, implantable organ stimulators such as nerve, bladder, sphincter and diaphragm stimulators, cochlear implants, prostheses, vascular grafts, self-expandable stents, balloon-expandable stents, stent-grafts, AV fistulas, grafts, PFO closure devices, arterial closure devices, artificial heart valves and cerebrospinal fluid shunts.

At present, preferred implantable medical devices for use with coatings of this invention are stents.

A stent refers generally to any device used to hold tissue in place in a patient's body. Particularly useful stents are those used for the maintenance of the patency of a vessel in a patient's body when the vessel is narrowed or closed due to diseases or disorders including, without limitation, tumors (in, for example, bile ducts, the esophagus or the trachea/bronchi), benign pancreatic disease, coronary artery disease, carotid artery disease, renal artery disease and peripheral arterial disease such as atherosclerosis, restenosis and vulnerable plaque. For example, a stent can be used to strengthen the wall of the vessel in the vicinity of a vulnerable plaque (VP). VP refers to a fatty build-up in an artery thought to be caused by inflammation. The VP is covered by a thin fibrous cap that can rupture leading to blood clot formation. Thus, a stent can not only maintain vessel patency but can act as a shield against VP rupture. A stent can be used in, without limitation, neuro, carotid, coronary, pulmonary, aortic, renal, biliary, iliac, femoral and popliteal as well as other peripheral vasculatures. A stent can be used in the treatment or prevention of disorders such as, without limitation, thrombosis, restenosis, hemorrhage, vascular dissection or perforation, vascular aneurysm, chronic total occlusion, claudication, anastomotic proliferation, bile duct obstruction and ureter obstruction.

In addition to the above uses, stents may also be employed for the localized delivery of therapeutic agents to specific treatment sites in a patient's body. Indeed, therapeutic agent delivery may be the sole purpose of the stent or the stent may be primarily intended for another use such as those discussed above with drug delivery providing an ancillary benefit.

A stent used for patency maintenance is usually delivered to the target site in a compressed state and then expanded to fit the vessel into which it has been inserted. Once at a target location, a stent may be self-expandable or balloon expandable. A stent coating must be flexible and capable of elongation.

Examples of stent materials include stainless steel, nitinol, tantalum, tantalum alloy, titanium, titanium alloy, cobalt chromium alloys, cobalt nickel alloys, platinum modified stainless steel, nickel-titanium-platinum alloys, niobium, niobium alloy, zirconium and zirconium alloy.

It is to be understood that an implantable medical device of the invention will have coated on it's surface at least one layer of a biologically compatible coating of the invention, although any number of coating layers are encompassed by the invention.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A biodegradable coating comprising a functionalized biodegradable polymer having the formula:

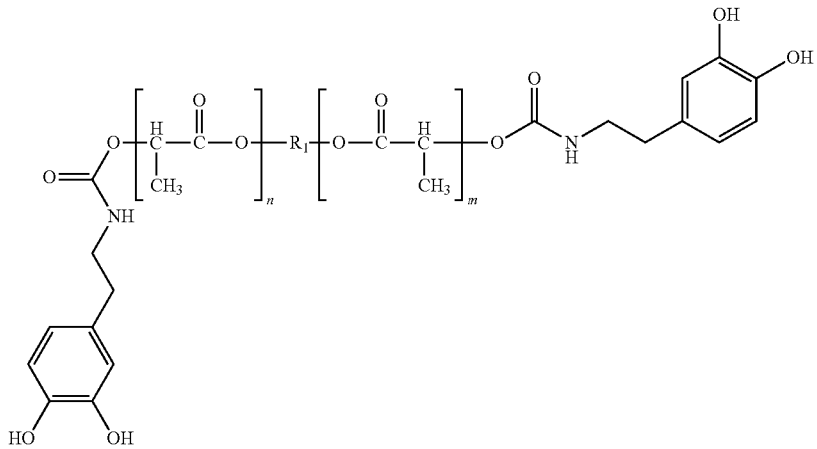

wherein $R_1$ is a $C_2$-$C_{16}$ linear, branched, unsaturated, or cyclic hydrocarbon; m and n each are a positive integer.

2. An implantable medical device comprising the coating according to claim 1.

3. The implantable medical device of claim 2, which is a stent.

* * * * *

UNITED STATES PATENT AND TRADEMARK OFFICE
CERTIFICATE OF CORRECTION

| | | |
|---|---|---|
| PATENT NO. | : 8,791,171 B2 | Page 1 of 1 |
| APPLICATION NO. | : 12/023953 | |
| DATED | : July 29, 2014 | |
| INVENTOR(S) | : Pacetti | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1476 days.

Signed and Sealed this
Fifteenth Day of December, 2015

Michelle K. Lee
*Director of the United States Patent and Trademark Office*